(12) United States Patent
Higgins

(10) Patent No.: US 9,504,981 B2
(45) Date of Patent: Nov. 29, 2016

(54) METHODS FOR PURIFYING NUCLEIC ACIDS AND DEVICES THEREOF

(71) Applicant: True Health Diagnostics, LLC, Frisco, TX (US)

(72) Inventor: William Ross Higgins, Minneapolis, MN (US)

(73) Assignee: True Health Diagnostics LLC, Frisco, TX (US)

(*) Notice: Subject to any disclaimer, the term of this patent is extended or adjusted under 35 U.S.C. 154(b) by 42 days.

(21) Appl. No.: 14/278,910

(22) Filed: May 15, 2014

(65) Prior Publication Data

US 2014/0343268 A1    Nov. 20, 2014

Related U.S. Application Data

(60) Provisional application No. 61/823,740, filed on May 15, 2013, provisional application No. 61/863,678, filed on Aug. 8, 2013.

(51) Int. Cl.
| | |
|---|---|
| *B01D 21/00* | (2006.01) |
| *B01J 19/12* | (2006.01) |
| *B01L 9/00* | (2006.01) |

(52) U.S. Cl.
CPC ............ *B01J 19/12* (2013.01); *B01L 9/523* (2013.01); *B01J 2219/12* (2013.01); *B01L 2200/025* (2013.01); *B01L 2300/0829* (2013.01)

(58) Field of Classification Search
CPC ...... B01J 19/12; B01L 9/523; C12Q 1/6806; C12N 15/1013
See application file for complete search history.

(56) References Cited

U.S. PATENT DOCUMENTS

| | | | | |
|---|---|---|---|---|
| 4,102,649 A * | 7/1978 | Sasaki | ............... | B01F 11/0094 366/114 |
| 2001/0030906 A1* | 10/2001 | Friedman | ............ | B01F 11/0008 366/114 |
| 2002/0044495 A1* | 4/2002 | Friedman | ............ | B01F 11/0022 366/212 |
| 2003/0116497 A1* | 6/2003 | Carlson | ............... | B01J 19/0046 210/435 |
| 2004/0022677 A1* | 2/2004 | Wohlstadter | .......... | B01L 3/5085 422/52 |
| 2005/0142033 A1* | 6/2005 | Glezer | .................. | B01L 3/5085 422/400 |
| 2005/0272114 A1* | 12/2005 | Darzins | ................. | B82Y 30/00 435/25 |
| 2006/0024808 A1* | 2/2006 | Darzins | ..................... | C12N 9/14 435/195 |
| 2010/0047132 A1* | 2/2010 | Tajima | ................... | B01L 3/5085 422/400 |
| 2010/0200405 A1* | 8/2010 | Lenz | ..................... | B03C 1/0332 204/600 |

* cited by examiner

*Primary Examiner* — Jill Warden
*Assistant Examiner* — Brittany Fisher
(74) *Attorney, Agent, or Firm* — Perkins Coie LLP

(57) ABSTRACT

A nucleic acid purification device includes a housing and an adapter operatively attached to the housing. The adapter is configured to receive at least one well plate which includes a plurality of wells for receiving contents including at least a sample and a plurality of paramagnetic particles. The device also includes a motor disposed within the housing and configured to selectively move at least the adapter to thereby disrupt or shake the contents of the plurality of wells when the at least one well plate is received by the adapter. The device further includes at least one electromagnetic feature configured to selectively receive an electrical signal and thereby magnetize at least a portion of the plurality of paramagnetic particles when the plurality of paramagnetic particles are received by the plurality of wells and the at least one well plate is received by the adapter.

18 Claims, 2 Drawing Sheets

METHODS FOR PURIFYING NUCLEIC ACIDS AND DEVICES THEREOF

This application claims the benefit of U.S. Provisional Patent Application No. 61/863,678, filed on Aug. 8, 2013 and U.S. Provisional Patent Application No. 61/823,740, filed on May 15, 2013, each of which is hereby incorporated by reference in its entirety.

FIELD

This technology generally relates to nucleic acid purification and, more particularly, to improved methods and devices for extracting nucleic acids from samples with increased throughput.

BACKGROUND

Magnetic stands of varying shapes, sizes and strengths are commercially available from many vendors for use in magnetic particle based nucleic acid extractions. In extraction using magnetic stands, the nucleic acids remains in the same plate for all wash steps and are eluted from the magnetic particles at the last step. However, the plate must be moved to and from the magnetic stand depending on the step of the extraction and/or to and from the shaker for shaking/vortexing steps.

Alternative methods for nucleic acid extraction use an electromagnet. For example, the electromagnet can be used to move the magnetic particles (including nucleic acids bound thereto) from one wash plate to the next. Particles are released from the electromagnet into each new plate. The movement of plates between a magnetic stand and a shaker, and/or of magnetic particles between different plates, is a rate limiting step in the extraction process which reduces throughput.

SUMMARY

In an aspect, a nucleic acid purification device is disclosed which includes a housing and an adapter operatively attached to the housing. The adapter is configured to receive at least one well plate which includes a plurality of wells for receiving contents including at least a sample and a plurality of paramagnetic particles. The device also includes a motor disposed within the housing and configured to selectively move at least the adapter to thereby disrupt or shake the contents of the plurality of wells when the at least one well plate is received by the adapter. The device further includes at least one electromagnetic feature configured to selectively receive an electrical signal and thereby magnetize at least a portion of the plurality of paramagnetic particles when the plurality of paramagnetic particles are received by the plurality of wells and the at least one well plate is received by the adapter.

In another aspect an adapter apparatus for facilitating nucleic acid purification is disclosed. The adapter is configured to mount to a well plate shaker device and includes a first attachment device for receiving at least one well plate, the at least one well plate including a plurality of wells for receiving contents including at least a sample and a plurality of paramagnetic particles. The adapter further includes at least one electromagnetic feature configured to selectively receive an electrical signal and thereby magnetize at least a portion of the plurality of paramagnetic particles when the plurality of paramagnetic particles are received by the plurality of wells and the at least one well plate is received by the first attachment device.

In yet another aspect, a method for purifying nucleic acids is disclosed. The method includes introducing a sample including a plurality of nucleic acids and a plurality of paramagnetic particles to one or more of a plurality of wells of at least one well plate, wherein the at least one well plate is attached to an adapter coupled to a well plate shaker device. An electrical signal is provided to at least one electromagnetic feature of the adapter to thereby magnetize at least a portion of the plurality of paramagnetic particles and bind the plurality of paramagnetic particles to the plurality of nucleic acids. One or more buffers are introduced to the one or more of the plurality of wells of the at least one well plate. At least a portion of the plurality of nucleic acids is extracted to produce a purified nucleic acid composition.

With this technology, nucleic acids can be mixed, whether unbound or bound to magnetic particles, on a shaker unit without moving well plates with the nucleic acids, such as to a magnetic stand for example. Accordingly, nucleic acid purification processes can advantageously proceed with higher throughput, decreased extraction time, less user intervention, and reduced instrument wear caused by increased plate movement between devices.

DETAILED DESCRIPTION

Figure 1:
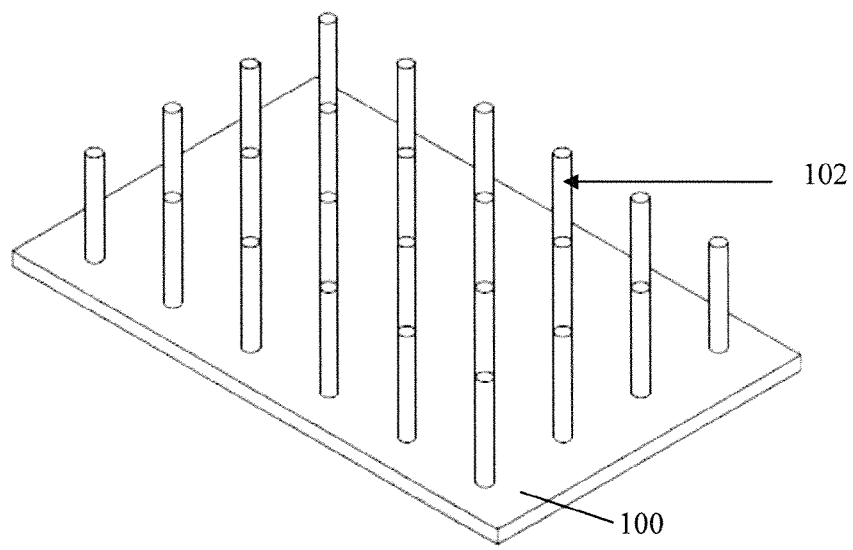
FIG. 1 is a perspective view of an exemplary adapter apparatus with an electromagnetic feature including a plurality of vertical projections.
Figure 2:
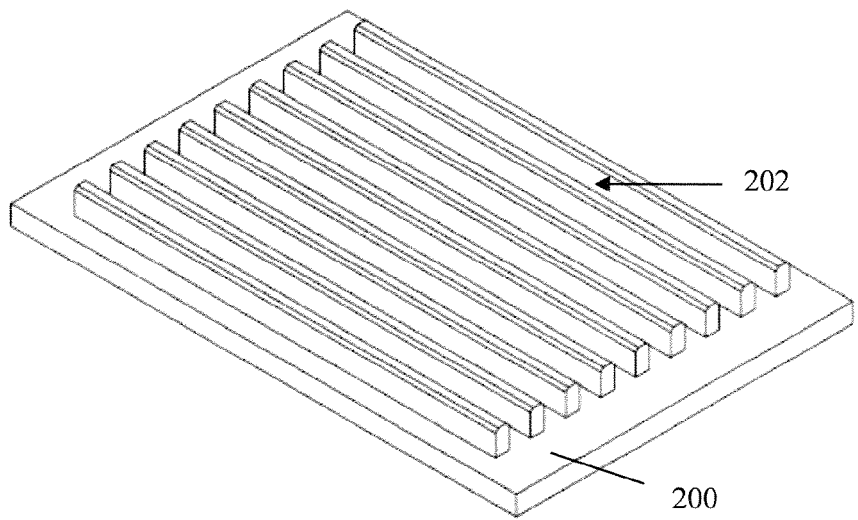
FIG. 2 is a perspective view of another exemplary adapter apparatus with an electromagnetic feature including a plurality of rails.

Referring to FIGS. 1 and 2, exemplary adapters 100 and 200 for facilitating nucleic acid purification are illustrated. In this example, the adapters 100 and 200 are each configured to receive at least one well plate at a first attachment device, optionally at a top portion. The well plate includes a plurality of wells for receiving contents including at least a sample, including nucleic acids to be extracted, and a plurality of paramagnetic particles. The adapters 100 and 200 are also configured to attach to a housing of a well plate shaker device of a liquid handling system, for example, or any other device including a motor disposed within a housing and configured to selectively move at least one of the adapters 100 and 200 to thereby disrupt or shake the contents of the wells.

The adapters 100 and 200 in this example include at least one electromagnetic feature configured to selectively receive an electrical signal and thereby magnetize at least a portion of the plurality of paramagnetic particles when the paramagnetic particles are received by the wells and the well plate is received by the first attachment device, as described and illustrated in more detail later. The electromagnetic feature can include a ferromagnetic material at least partially surrounded by an electrically conductive material, although other types of materials can also be used.

Optionally, the adapters 100 and 200 include a diamagnetic material, although other types of materials can also be used. In some examples, the adapters 100 and 200 optionally include a top portion and the electromagnetic feature can be disposed proximate the top portion and between the top portion and the well plate and/or the electromagnet feature can be integrated with the adapter as a single unit, for example.

For example, the electromagnetic feature can include a substantially planar top surface configured to be disposed adjacent to a bottom portion of the well plate. In these examples, the electromagnetic feature is configured to produce a magnetic field in a direction substantially perpendicular to the bottom portion of the well plate and a top surface of at least one of the adapters 100 and 200 when the electromagnetic feature receives an electrical signal.

Referring more specifically to FIG. 1, in one example, the adapter 100 includes an electromagnet feature including a plurality of protrusions 102 extending away from a top portion of the adapter 100 and between at least a portion of the plurality of wells. In another example, the at least one electromagnetic feature includes a plurality of depressions and is positioned between at least a portion of the wells. Referring more specifically to FIG. 2, in yet another example, the adapter 200 includes an electromagnetic feature including a plurality of rails 202 extending away from a top portion of the adapter 200.

In order to receive the electrical signal, the electromagnet feature optionally includes an electrical interface coupled to a switch of the well plate shaker device to which the adapter is configured to attach. The switch is electrically connected to an electrical signal source and configured to operatively supply the electrical signal to the electromagnetic feature when engaged by a user or a controller programmed by the user to supply the electrical signal to the electromagnetic feature at one or more selected times.

Figure 3:
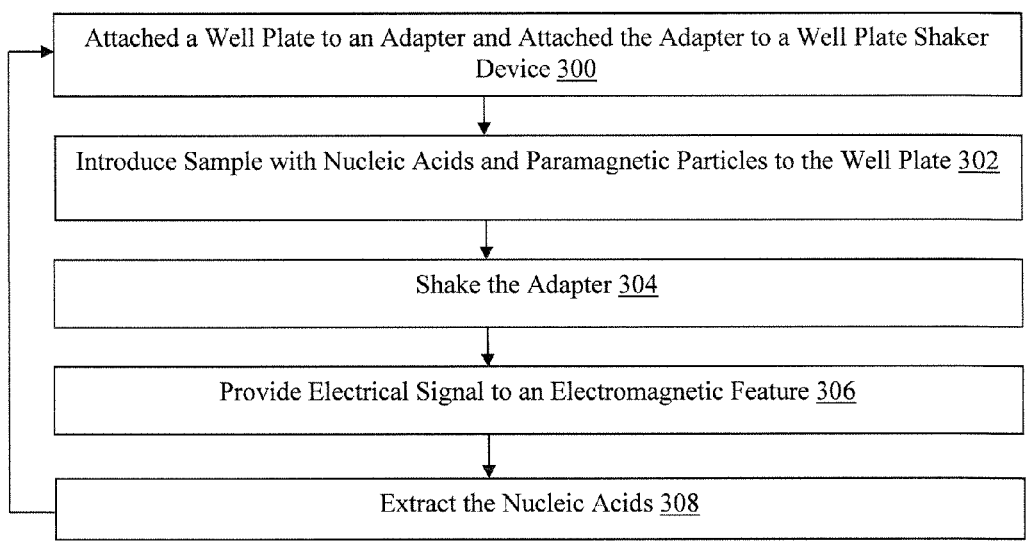
FIG. 3 is an exemplary method for purifying nucleic acids.

Referring to FIG. 3, an exemplary method for purifying nucleic acids will now be described. In step 300 in this example, a well plate is securely attached to an adapter, such as adapter 100 for purposes of this example only although any other type of adapter with an electromagnetic feature can also be used. Additionally, in step 300, the adapter 100 is coupled to a well plate shaker device and connected to an electrical interface.

In step 302, a sample with nucleic acids, such as a human sample (e.g., blood) is introduced to one or more wells of the well plate. Additionally, paramagnetic particles are introduced to the one or more wells of the well plate, as is known in the art and will not be described in detail herein.

In step 304, the adapter 100 is shaken by the well plate shaker device to thereby mix the sample and the plurality of paramagnetic particles while the plurality of nucleic acids are unbound from the plurality of paramagnetic particles to thereby increase the effectiveness of the particle binding.

In step 306, an electrical signal is provided to the electromagnetic feature of the adapter 100 to thereby magnetize at least a portion of the paramagnetic particles and bind the paramagnetic particles to the nucleic acids in the sample.

In step 308, at least a portion of the nucleic acids in the sample are extracted to produce a purified nucleic acid composition. The nucleic acids can be extracted by introducing one or more buffers, such as at least one wash and/or elution buffer for example, to the one or more well plates and subsequently switching off the electrical signal previously supplied to the electromagnetic feature to thereby unbind the paramagnetic particles from the nucleic acids in the sample.

By this technology, nucleic acids can be extracted from a sample without removing the well plate from the adapter or the well plate shaker device. Accordingly, the rate limiting step is not required and an increased number of samples can advantageously be processed in a reduced time period.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A nucleic acid purification device, comprising:
   a housing and an adapter operatively attached to the housing, the adapter configured to receive at least one well plate, the at least one well plate comprising a plurality of wells for receiving contents including at least a sample and a plurality of paramagnetic particles;
   a motor disposed within the housing and configured to selectively move at least the adapter to thereby disrupt or shake the contents of the plurality of wells when the at least one well plate is received by the adapter; and
   at least one electromagnetic feature disposed between a top portion of the adapter and the at least one well plate or disposed adjacent to a bottom portion of the at least one well plate, wherein the at least one electromagnetic feature is configured to selectively receive an electrical signal and thereby magnetize at least a portion of the plurality of paramagnetic particles when the plurality of paramagnetic particles are received by the plurality of wells and the at least one well plate is received by the adapter.

2. The device of claim 1 wherein the adapter is further configured to receive the at least one well plate securely and at a top portion of the adapter.

3. The device of claim 1 wherein the at least one electromagnetic feature comprises a plurality of protrusions extending away from a top portion of the adapter or a plurality of depressions and is positioned between at least a portion of the plurality of wells.

4. The device of claim 1 wherein the at least one electromagnetic feature comprises a substantially planar top surface configured to be disposed adjacent to a bottom portion of the at least one well plate.

5. The device of claim 4 wherein the at least one electromagnetic feature is configured to produce a magnetic field in a direction substantially perpendicular to the bottom portion of the at least one well plate when the electromagnetic feature receives the electrical signal.

6. The device of claim 1 further comprising a switch electrically connected to an electrical signal source, the switch configured to selectively supply the electrical signal to the at least one electromagnetic feature when engaged by a user or a controller programmed by the user to supply the electrical signal to the at least one electromagnetic feature at one or more selected times.

7. The device of claim 1 wherein the electromagnetic feature comprises a ferromagnetic material at least partially surrounded by an electrically conductive material.

8. The device of claim 1 wherein the at least one electromagnetic feature is configured to be disposed between the adapter and the at least one well plate, the adapter comprises at least one diamagnetic material, and the at least one electromagnetic feature is configured to produce a magnetic field in a direction substantially perpendicular to a top surface of the adapter when the electromagnetic feature receives the electrical signal.

9. An adapter apparatus for facilitating nucleic acid purification, the adapter configured to mount to a well plate shaker device and comprising:
- a first attachment device for receiving at least one well plate, the at least one well plate comprising a plurality of wells for receiving contents including at least a sample and a plurality of paramagnetic particles;
- at least one electromagnetic feature disposed proximate a top portion of the apparatus, between the top portion and the at least one well plate or disposed adjacent to a bottom portion of the at least one well plate, wherein the at least one electromagnetic feature is configured to selectively receive an electrical signal and thereby magnetize at least a portion of the plurality of paramagnetic particles when the plurality of paramagnetic particles are received by the plurality of wells and the at least one well plate is received by the first attachment device.

10. The apparatus of claim 9 wherein the at least one electromagnetic feature comprises a plurality of protrusions extending away from a top portion of the adapter and between at least a portion of the plurality of wells.

11. The apparatus of claim 9 wherein the at least one electromagnetic feature comprises a substantially planar top surface configured to be disposed adjacent to a bottom portion of the at least one well plate.

12. The apparatus of claim 11 wherein the at least one electromagnetic feature is configured to produce a magnetic field in a direction substantially perpendicular to the bottom portion of the at least one well plate when the electromagnetic feature receives the electrical signal.

13. The apparatus of claim 9 wherein the at least one electromagnetic feature further comprises an electrical interface coupled to a switch of the well plate shaker device, the switch electrically connected to an electrical signal source and configured to operatively supply the electrical signal to the at least one electromagnetic feature.

14. A method for purifying nucleic acids, the method comprising:
- combining a plurality of nucleic acids and a plurality of paramagnetic particles in one or more of a plurality of wells of at least one well plate, wherein the at least one well plate is attached to an adapter coupled to a well plate shaker device;
- binding at least a portion of the nucleic acids to at least a portion of the paramagnetic particles to produce nucleic acid-paramagnetic particle complexes;
- providing an electrical signal to at least one electromagnetic feature of the adapter to thereby magnetize at least a portion of the nucleic acid-paramagnetic particle complexes;
- introducing one or more buffers to the one or more of the plurality of wells of the at least one well plate; and
- extracting at least a portion of the plurality of nucleic acids to produce a purified nucleic acid composition;
- wherein the steps are performed without removing the well plate from the adapter or the well plate shaker device.

15. The method of claim 14 further comprising shaking the adapter with the well plate shaker device to thereby mix the plurality of nucleic acids and the plurality of paramagnetic particles when the plurality of nucleic acids are unbound from and bound to the plurality of paramagnetic particles.

16. The method of claim 15 wherein the steps are repeated for a plurality of well plates to thereby provide increased throughput.

17. The method of claim 14 further comprising introducing at least one wash buffer or at least one elution buffer subsequent to providing the electrical signal to the at least one electromagnetic feature.

18. The method of claim 14 further comprising, prior to providing the electrical signal to the at least one electromagnetic feature, the steps of:
- coupling the adapter to the well plate shaker device at an electrical interface; and
- securely attaching the at least one well plate to the adapter.

* * * * *